US008852172B2

(12) United States Patent
Dijksman et al.

(10) Patent No.: US 8,852,172 B2
(45) Date of Patent: Oct. 7, 2014

(54) INGESTIBLE ELECTRONIC CAPSULE AND IN VIVO DRUG DELIVERY OR DIAGNOSTIC SYSTEM

(75) Inventors: Johan Frederik Dijksman, Weert (NL); Frits Tobi De Jongh, Beek en Donk (NL); Michel Gerardus Pardoel, Mierlo (NL); Claude Jean-Marie Malaurie, Mondeville (FR); Yvan O. J. G. Droinet, Douvres-la-Delivrande (FR); Anke Pierik, Eindhoven (NL); Judith Margreet Rensen, Eindhoven (NL); Jeff Shimizu, Cortlandt Manor, NY (US); Hans Zou, Windsor, NJ (US); Remus Albu, Forest Hills, NY (US)

(73) Assignee: Medimetrics Personalized Drug Delivery, Eindhoven (NL)

( * ) Notice: Subject to any disclaimer, the term of this patent is extended or adjusted under 35 U.S.C. 154(b) by 1014 days.

(21) Appl. No.: 12/515,424

(22) PCT Filed: Nov. 5, 2007

(86) PCT No.: PCT/IB2007/054481
§ 371 (c)(1),
(2), (4) Date: May 19, 2009

(87) PCT Pub. No.: WO2008/062333
PCT Pub. Date: May 29, 2008

(65) Prior Publication Data
US 2010/0049012 A1 Feb. 25, 2010

Related U.S. Application Data

(60) Provisional application No. 60/866,637, filed on Nov. 21, 2006.

(51) Int. Cl.
*A61B 5/07* (2006.01)
*A61B 1/04* (2006.01)
*A61B 5/00* (2006.01)
*A61B 1/00* (2006.01)

(52) U.S. Cl.
CPC ............. *A61B 5/073* (2013.01); *A61B 1/00016* (2013.01); *A61B 1/041* (2013.01); *A61B 5/4839* (2013.01)
USPC ....................................................... 604/890.1

(58) Field of Classification Search
None
See application file for complete search history.

(56) References Cited

U.S. PATENT DOCUMENTS 4,239,040 A * 12/1980 Hosoya et al. ................ 604/135
4,844,076 A * 7/1989 Lesho et al. .................. 600/302
(Continued)

FOREIGN PATENT DOCUMENTS

EP 1398052 A2 3/2004
EP 1602318 A1 12/2005
(Continued)

OTHER PUBLICATIONS

Khandpur (Printed Circuit Boards 2005, Tata McGraw-Hill pp. 427 and 428).*

(Continued)

*Primary Examiner* — Ernst V Arnold
(74) *Attorney, Agent, or Firm* — Lee & Hayes, PLLC

(57) ABSTRACT

An ingestible electronic capsule (100) for introduction into the bodily lumen comprises a circuit board with at least one electronic component (4, 5, 7, 8, 9, 11, 12, 13, 14). The circuit board is formed from a flex foil (10), thereby reducing the number of components and improving the robustness and reliability of the ingestible electronic capsule (100).

20 Claims, 3 Drawing Sheets

(56) References Cited

U.S. PATENT DOCUMENTS

| | | | | |
|---|---|---|---|---|
| 5,792,048 | A * | 8/1998 | Schaefer | 600/302 |
| 6,242,274 | B1 * | 6/2001 | Nyholm | 438/27 |
| 2004/0253304 | A1 | 12/2004 | Gross | |
| 2005/0090808 | A1 * | 4/2005 | Malave et al. | 604/890.1 |
| 2005/0143623 | A1 | 6/2005 | Kojima | |
| 2006/0224040 | A1 | 10/2006 | Khait et al. | |

FOREIGN PATENT DOCUMENTS

| | | | |
|---|---|---|---|
| EP | 1698267 | A1 | 9/2006 |
| EP | 1707102 | A1 | 10/2006 |
| JP | 2001091860 | | 4/2001 |
| JP | 2005006769 | | 1/2005 |
| JP | 2005185567 | | 7/2005 |
| JP | 2005205078 | | 8/2005 |
| JP | 2006280954 | | 10/2006 |
| WO | 02102224 | A2 | 12/2002 |
| WO | 2006070360 | A1 | 7/2006 |

OTHER PUBLICATIONS

Macleod (PRIME Faraday Partnership Flexible Circuit Technology Jun. 2002 pp. 1-54; 59 total pages).*
Engelbrecht (Connecting Medical Informatics and Bio-Informatics: Proceedings of Mie2005: The Xixth International Congress of the European Federation for Medical Informatics, 2005, pp. 247 and 250). 2 pages.*
Oblique [online] retrieved on May 21, 2014 from: http://www.merriam-webster.com/dictionary/oblique; 1 page.*
The Chinese Office Action mailed May 20, 2013 for Chinese patent application No. 200780043250.1, a counterpart foreign application of U.S. Appl. No. 12/515,424, 14 pages.
Teh Chinese Office Action mailed Sep. 27, 2013 for Chinese patent application No. 200780043250.1, a counterpart foreign application of U.S. Appl. No. 12/515,424, 25 pages.
The Japanese Office Action mailed Oct. 22, 2013 for Japanese patent application No. 2009-536826, a counterpart foreign application of U.S. Appl. No. 12/515,424, 5 pages.
The European Office Action mailed Apr. 17, 2014 for European patent application No. 07826979.2, a counterpart foreign application of U.S. Appl. No. 12/515,424, 3 pages.

* cited by examiner

INGESTIBLE ELECTRONIC CAPSULE AND IN VIVO DRUG DELIVERY OR DIAGNOSTIC SYSTEM

The invention relates to an ingestible electronic capsule for introduction into a bodily lumen, comprising a circuit board on which at least one electronic component is mounted. The invention also relates to an in vivo drug delivery or diagnostic system.

Ingestible electronic capsules or pills for introduction into a bodily lumen are known and for example used for drug release and for diagnosis of the gastrointestinal (GI) tract in the human or animal body. Electronic pills for drug release typically have a housing made from bio-compatible materials that houses both a medicament reservoir containing a pre-dosed amount of a medicament and control electronics for precisely delivering the medicament to a pre-selected site in the GI tract of a human or animal. Also contained by the housing is a means for providing a link for wireless communication by the pill to the outside of the body upon ingestion of the pill by a subject. The electronics enable the pill to deliver the on board medicament at a specific site in the gastrointestinal tract of a human or animal using sensors, timing or location. An ingestible electronic capsule or pill for diagnosis of the GI track typically comprises a sensor (and typically not a drug reservoir) that monitors a body temperature or a pH value, and/or comprises an image sensor that is arranged to create images of the GI tract.

WO 02/102224 discloses an in vivo sensing device for diagnostic purposes such as for imaging the GI tract. The in vivo sensing device comprises at least one image sensor and a circuit board having a plurality of rigid sections and a plurality of flexible sections, wherein the image sensor and the control electronics are disposed on rigid sections of the circuit board. The circuit board may be folded into a housing configured for in vivo sensing.

A disadvantage of the known ingestible electronic capsule is that the ingestible electronic capsule comprises many components thereby decreasing the robustness and reliability of the ingestible electronic capsule.

It is an object of the invention to provide an ingestible electronic capsule, which is more robust and reliable. The invention is defined by the independent claims. Advantageous embodiments are defined by the dependent claims.

This object is achieved by the ingestible electronic capsule according to the invention, which is characterized in that the circuit board is formed from a flex foil. By providing an ingestible electronic capsule with a circuit board formed from a flex foil, which does not comprise separate rigid sections, the number of components in the ingestible electronic capsule is reduced thereby improving the robustness and reliability of the capsule.

This object is also achieved by the in vivo drug delivery or diagnostic system comprising an ingestible electronic capsule according to the invention and an external device arranged to communicate with the at least one electronic component.

In an embodiment of the ingestible electronic capsule according to the invention, at least one electronic component is integrated in the flex foil. This further reduces the number of separate components in the capsule. In a preferred embodiment, an antenna is integrated in the flex foil.

In an embodiment of the ingestible electronic capsule according to the invention, the at least one electronic component is attached to the flex foil with a solder bump providing for a robust and reliable electrical attachment of the at least one electronic component to the flex foil. In a further embodiment of the ingestible electronic capsule according to the invention, at least part of remaining open space between the flex foil and the at least one electronic component is filled with a moldable resin. This provides for a robust and reliable fixation of the at least one electronic component to the flex foil.

In an embodiment of the ingestible electronic capsule according to the invention, a power supply unit is mounted on the flex foil with a conducting adhesive. This provides for a robust and reliable electrical attachment of the power supply unit to the flex foil.

In an embodiment of the ingestible electronic capsule according to the invention, the flex foil is bended along at least one bending line. This way the flex foil allows for an optimum filling of the capsule.

In an embodiment of the ingestible electronic capsule according to the invention, the ingestible electronic capsule comprises a system in package with a microprocessor, a transceiver, a sensor and a passive electronic device. The integration of several electronic components in the system in package further increases the robustness of the capsule.

In an embodiment of the ingestible electronic capsule according to the invention, the ingestible electronic capsule further comprises a drug reservoir and a movable piston for emptying the drug reservoir, which movable piston is electrically and mechanically connected to the flex foil. In this way the flex foil allows for a free movement of the movable means.

BRIEF DESCRIPTION OF THE SEVERAL VIEWS OF THE DRAWINGS

These and other aspects of the invention will be further elucidated and described with reference to the drawings, in which.

The Figures are not drawn to scale. In general, identical components are denoted by the same reference numerals in the figures.

Implementations of ingestible electronic capsules having a drug delivery system in combination with a diagnostic system will be explained below as an example. However, the invention is not limited to these examples and may also be applied in ingestible electronic capsules that serve other purposes.

Figure 1:
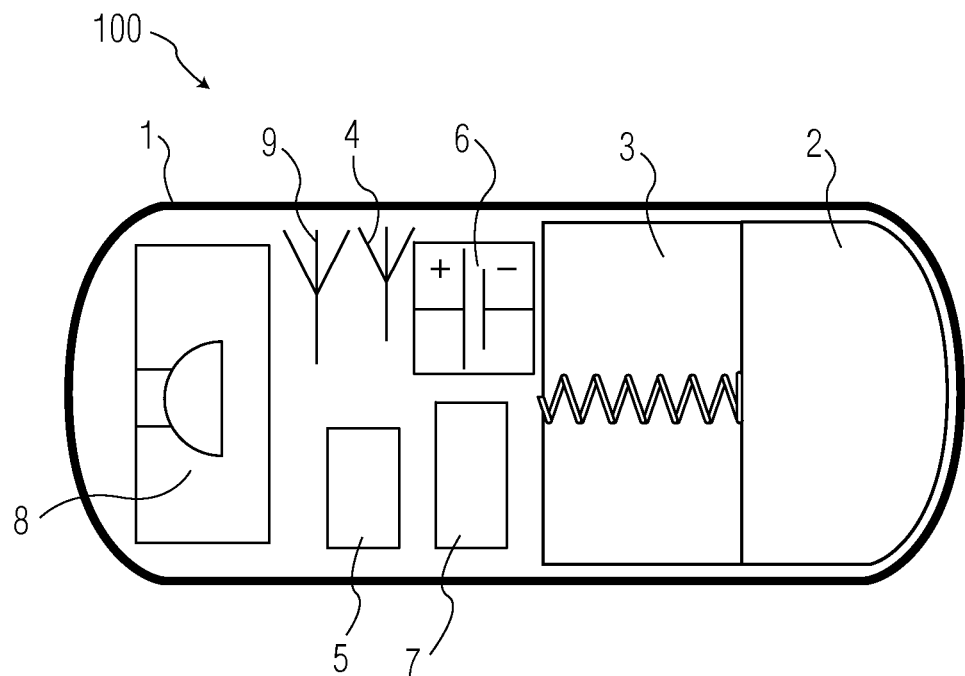
FIG. 1 is a schematic cross-sectional view of an embodiment of an ingestible electronic device according to the invention.

FIG. 1 is a schematic diagram of an ingestible electronic capsule 100 with electronic control circuitry, a drug delivery system and sensors for diagnostic purposes. The ingestible electronic capsule 100 comprises a cylindrical housing 1 in which, amongst others, the electronic control circuitry, the drug delivery system and the sensors for diagnostic purposes are mounted. Housing 1 is preferably made from bio-compatible materials such that capsule 100 is bio-compatible for at least the amount of time it requires to traverse the GI tract of a human or animal. The bio-compatible materials are preferably stable at room temperature and below room temperature, such that capsule 100 has a long shelf life. Housing 1 may be fabricated from a biologically safe polymeric material such as, for example, polytetrafluoroethylene, polypropylene, polyethylene, acrylics and the like. Housing 1 is more preferably manufactured from materials used to fabricate implantable devices, including pacemaker leads and cardiac prosthesis devices, such as artificial hearts, heart valves, intra-aortic balloons, and ventricular assist devices. Assembled capsule 100 is preferably sized to be suitable to be swallowed by a human or animal. Preferably, assembled capsule 100 is about 1 cm in diameter and 2 to 3 cm long.

A drug reservoir 2 is used for storing a drug or drug that can be delivered to the GI tract inside the human body via a, not shown, dispensing hole in the capsule 1. The drug reservoir 2 is emptied via the dispensing hole with the aid of a release mechanism 3. The release mechanism comprises a movable piston to enable the emptying of the drug reservoir 2. The piston may be driven by, for example, a linear motor and is controlled by a built-in microprocessor 7. A sensor 8, such as for monitoring a pH value, is also provided in the ingestible electronic capsule 100. A power source 6, in this case a battery, powers the electronic control circuitry in order for each of the mechanical and electronic components to operate. For a long shelf life it is essential that the electronic control circuitry is completely decoupled from the power source 6, otherwise a small leakage current will ultimately empty the power source 6. To start the electronic pill it must be waked-up. For that purpose a wake-up circuit (not shown) may be designed that is powered from the outside by inductive radiation that is received by a first antenna 4. The electrical connections between the electronic components 4,5,7,8, the power source 6 and the release mechanism 3 are not shown in FIG. 1. Other electronic components for diagnostic purposes that may be placed inside the housing 1 are for example a temperature sensor and an image sensor. Further electronic components that are part of the electronic control circuitry in the capsule 100 may be capacitors, coils, resistors, etc.

A transceiver 5 and a second antenna 9 provide for an RF link and are used for transmitting signals to and receiving signals from outside of the ingestible electronic capsule 100. For example, the transceiver 5 and the second antenna 9 communicate with a portable device (not shown), which is able to program a drug release profile by transmitting a signal that is subsequently received by the second antenna 9 and the transceiver 5. The portable device may also communicate with a base station (not shown) with, for example, an infrared link, which base station is used for communication with, for example, a medical expert.

Figure 2:
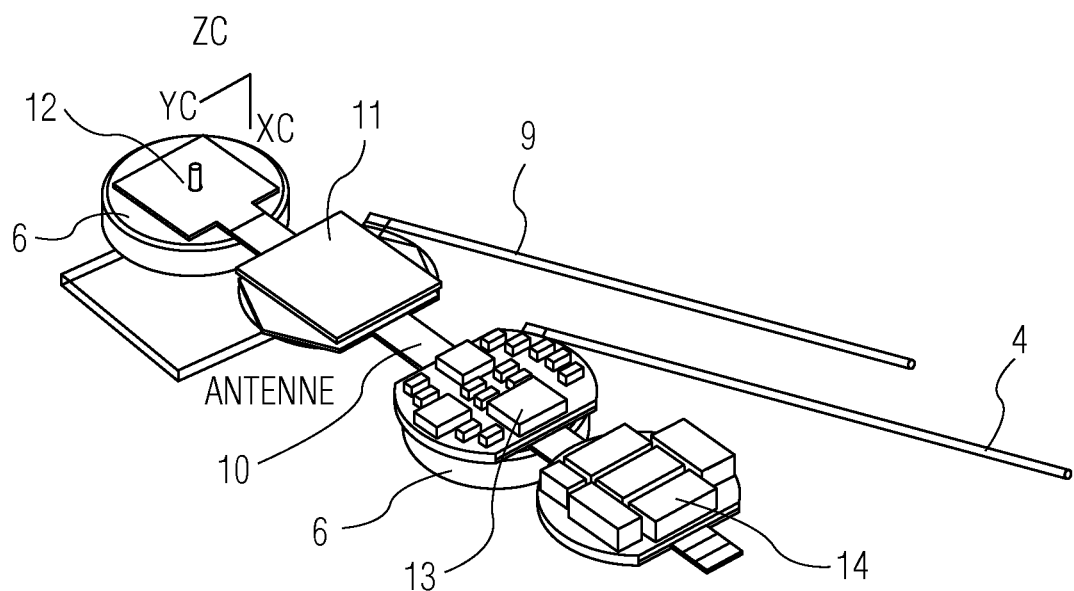
FIG. 2 is a perspective view of a flex foil including various electronic components.

As is illustrated in FIG. 1, the housing 1 comprises a large number of electronic components that need to be mutually electrically connected. As is shown in FIG. 2, one continuous flex foil 10 is applied to provide for a printed circuit board on which various electronic components are attached. The attachment of various electronic components on the flex foil 10 and the integration of electrical connections between the electronic components on the flex foil 10 reduces the number of components and hence increases the reliability of the capsule 100.

The flex foil 10 is made of a polyimide substrate such as Kapton™. The flex foil 10 has a large width on locations where first, second, third and fourth electronic components 11,12,13,14 and power source 6 are placed on the flex foil 10, and has a small width in between the locations where the first, second, third and fourth electronic components 11,12,13,14 and the power source 6 are placed on the flex foil 10. The small width sections of the flex foil 10 comprise electrical wiring formed of, for example, copper lines to interconnect the first, second, third and fourth electronic components 11,12,13,14. In this example there are two power sources 6 that are both attached to the flex foil 10 using a conductive adhesive material or paste, such as an electrically conductive silicone adhesive or an electrically conductive tape. Individual devices that are part of the first, second, third and fourth electronic components 11,12,13,14 are attached to the flex foil 10 with a solder bump technology (Ball Grid Array) thereby providing for an electrical contact from each device of the first, second, third and fourth electronic component 11,12,13,14 to the copper lines of the flex foil 10. In this way a contacting surface of each device of the first, second, third and fourth electronic component 11,12,13,14 faces a contacting surface of the flex foil 10. The space that is in between the contacting surface of the flex foil 10 and the contacting surface of each device of the first, second, third and fourth electronic component 11,12,13,14 is filled, at least partially, with a moldable resin to achieve a strong fixation of each device of the first, second, third and fourth electronic component 11,12,13,14 to the flex foil 10.

In this example, the first electronic component 11 comprises a system in package (SIP), which houses, in addition to the required electrical connections, the transceiver 5, the microprocessor 7, a temperature sensor and several passive devices, such as capacitors, transistors and/or resistors. The SIP is attached to the flex foil 10 with the solder bump technology. The second electronic component 12 comprises, in this example, a pH sensor including control electronics. The third and fourth electronic components 13 and 14 comprise various electronic devices that cannot be integrated in a semi-conductor circuit, such as a capacitor and/or a coil. These various electronic devices are each individually attached to the flex foil with the bump technology.

A further reduction of the number of components in the capsule 100 is achieved by the integration of the first antenna 4 and the second antenna 9 in the flex foil. As is shown in FIG. 2, the first antenna 4 and the second antenna 9 are formed from a portion of the flex foil 10 on which an electrically conducting layer is integrated. In this way the first antenna 4 and the second antenna 9 are integrated in the flex foil 10 and therefore bendable allowing for a more optimized filling of the housing 1.

Another advantage of the flex foil 10 is the easy removal of a portion of the flex foil 10. For example, a socket may be attached via a side arm of the flex foil 10 to the microprocessor 7. The side arm comprises metal lines that provide for an electrical connection between the microprocessor 7 and the socket. By attaching a plug to this socket, the microprocessor 7 can be programmed in an easy way in the factory without using the RF link and/or the battery 6. After the programming is finished, the side arm of the flex foil 10 including the socket is not needed anymore, and the side arm can be removed, including the socket, by, for example, simple cutting the side arm. The socket may also be used to check various functions of, for example, the microprocessor 7, the transceiver 5, the sensor 8 and other electronic control circuitry.

Figure 3:
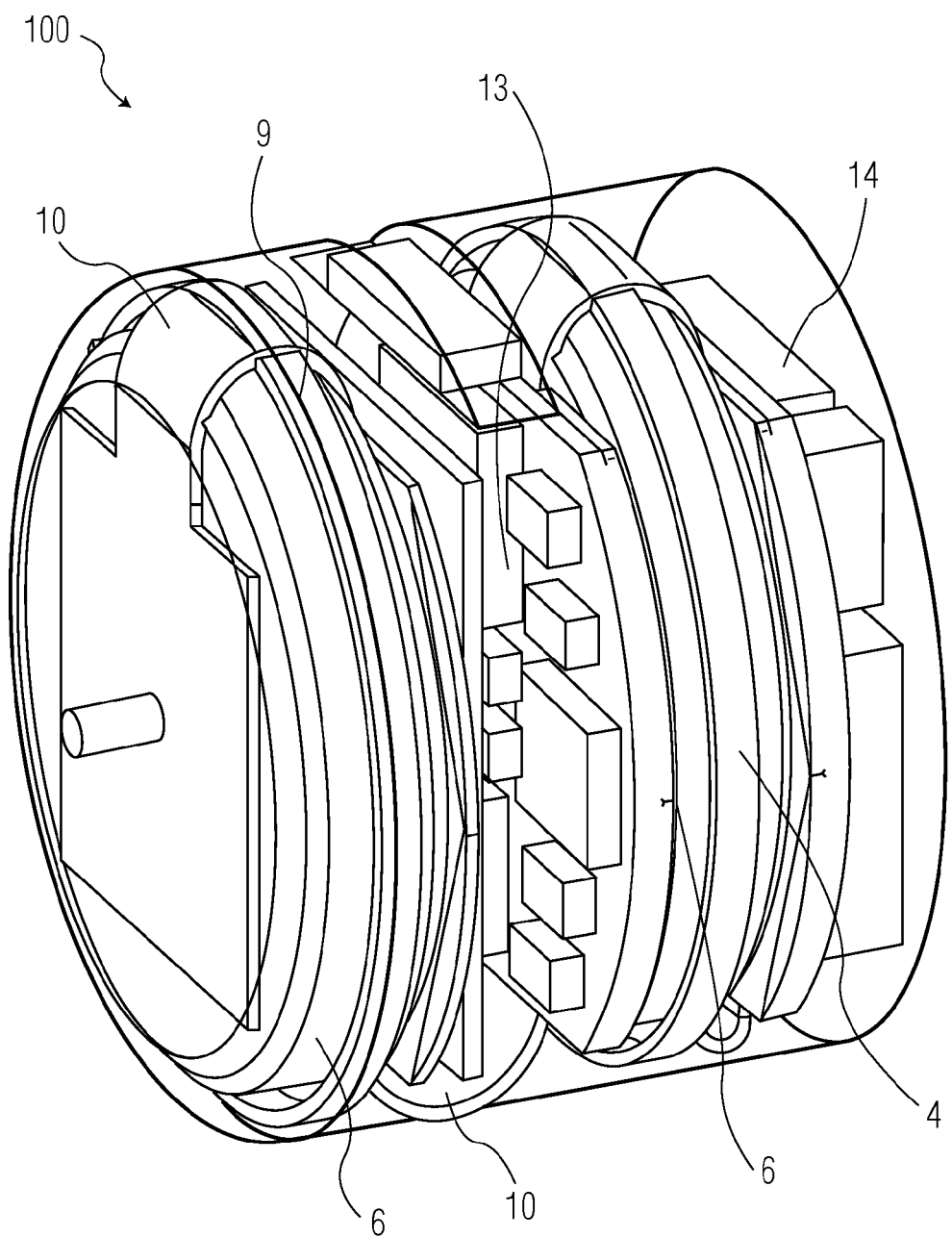
FIG. 3 is a perspective cross-sectional detailed view of a part of an embodiment of an ingestible electronic device according to the invention.
Figure 4:
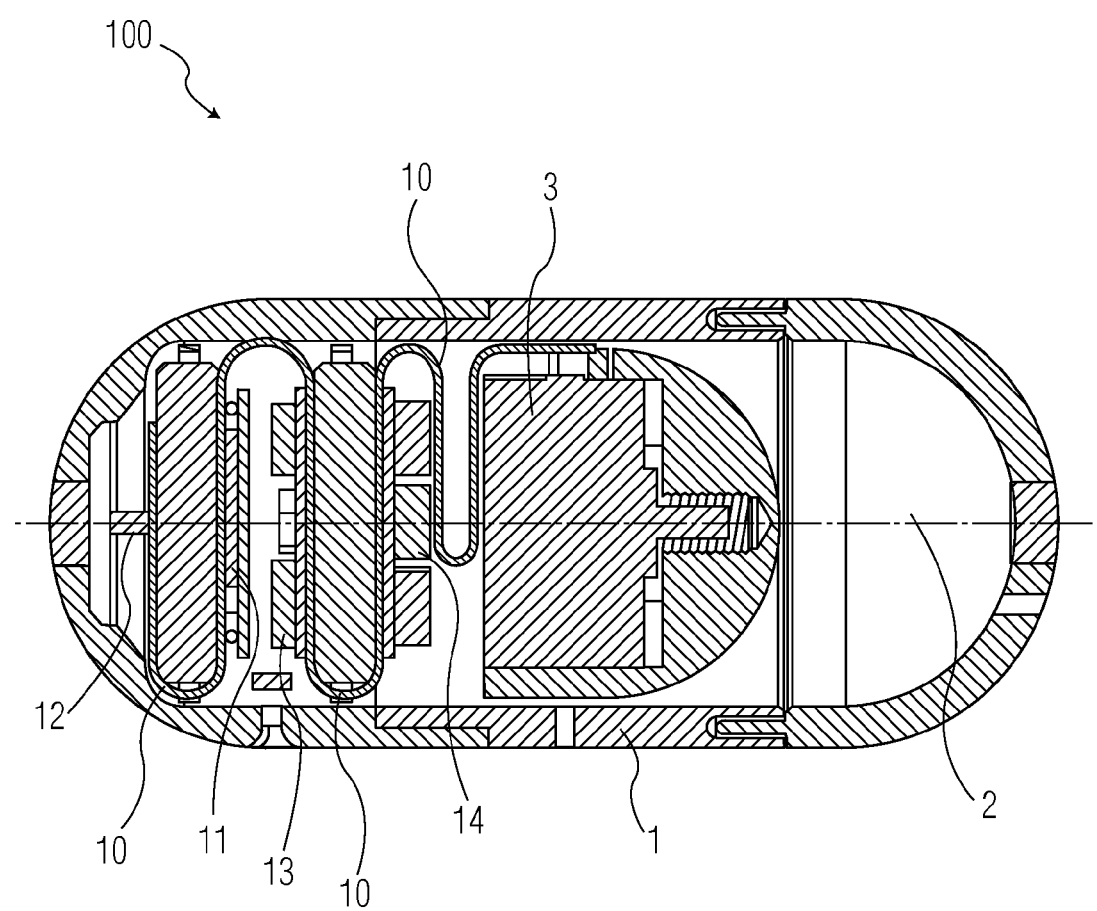
FIG. 4 is a cross-sectional view of an embodiment of an ingestible electronic device according to the invention.

FIG. 3 illustrates a cross-sectional detailed view of a part of an embodiment of the ingestible electronic capsule 100 according to the invention and FIG. 4 shows a cross-sectional view of the same embodiment of the ingestible electronic capsule 100 according to the invention along a plane mainly parallel to FIG. 3. FIG. 3 and FIG. 4 show a printed circuit board that is formed from the one-piece continuous flex foil 10. The flex foil 10, comprising the various electronic components and devices, is bended or folded along several folding lines to enable an optimum filling of the electronic components in the housing 1. The first antenna 4 and the second antenna 9 are bended such that they comprise the appropriate amount of turns for an optimum functionality, such as for example in the order of two turns.

The flex foil 10 is electrically and mechanically attached to the release mechanism 3, which is intended to release a drug from the drug reservoir 2 via the dispensing hole into the intestines of the human or animal body. The flex foil 10 is folded along at least one folding line when the release mechanism 3 is in the start position before the drug release is started. This folded situation of the flex foil 10 allows for the release mechanism 3 to move in a direction away from the flex foil 10 towards the drug reservoir 2 without being hampered in its movement by the flex foil 10. When the required amount of drug from the drug reservoir 2 is released by the movement of the release mechanism 3 in a direction away from the flex foil 10 towards the drug reservoir 2, the flex foil 10 is partially unfolded.

After assembly of the flex foil 10 in the housing 1, remaining open spaces may be filled with, for example, a moldable resin to strengthen the construction of the capsule 100. Of course, a part of the flex foil 10 that is intended to fold and unfold in association with the movable release mechanism 3, should not be fixed by the moldable resin.

In summary, the invention provides for an ingestible electronic capsule for introduction into the bodily lumen comprises a circuit board with at least one electronic component. The circuit board is formed from a flex foil, thereby reducing the number of components and improving the robustness and reliability of the ingestible electronic capsule.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of other elements or steps than those listed in a claim. The word "a" or "an" preceding an element does not exclude the presence of a plurality of such elements.

The invention claimed is:

1. An ingestible electronic capsule for introduction into a bodily lumen, comprising:
    a housing;
    a continuous flex foil formed of a uniform material and having a first portion extending generally in a longitudinal direction, the flex foil further having a second portion that extends from the first portion at an angle relative to the longitudinal direction;
    an electrically conducting layer integrated into the second portion;
    a plurality of electronic components disposed directly on the flex foil and spaced from each other along the longitudinal direction on the first portion, the continuous flex foil being bent along at least one bend line disposed in the lateral direction between adjacent electronic components to form a bent flex foil and the second portion being bent relative to the first portion;
    a reservoir sealed relative to the first portion of the housing, the reservoir containing a drug for expulsion from the capsule via a dispensing hole; and
    a release mechanism movable to empty the drug through the dispensing hole, the release mechanism being electrically connected to at least one of the plurality of electronic components formed on the flex foil.

2. The ingestible electronic capsule according to claim 1, wherein the electrically conducting layer is an antenna.

3. The ingestible electronic capsule according to claim 2, wherein the antenna is wrapped around a remainder of the flex foil.

4. The ingestible electronic capsule according to claim 1, wherein the at least one electronic component is attached to the flex foil with a solder bump.

5. The ingestible electronic capsule according to claim 4, wherein at least part of remaining open space between the flex foil and the at least one electronic component is filled with a moldable resin.

6. The ingestible electronic capsule according to claim 1, wherein a power supply unit is mounted on the flex foil with a conducting adhesive.

7. The ingestible electronic capsule according to claim 1, wherein the flex foil is bended along at least one bending line.

8. The ingestible electronic capsule according to claim 1, wherein the ingestible electronic capsule comprises a system in package with a microprocessor a transceiver, a sensor and a passive electronic device.

9. The ingestible electronic capsule according to claim 1, wherein the release mechanism is a movable piston for emptying the drug reservoir, which movable piston is electrically and mechanically connected to the flex foil.

10. In vivo drug delivery or diagnostic system comprising an ingestible electronic capsule according to claim 1 and an external device arranged to communicate with the at least one electronic component.

11. The ingestible capsule of claim 1, further comprising a socket configured to receive a plug, wherein the flex foil includes a side arm electrically connecting the socket to the flex foil.

12. The ingestible capsule of claim 11, wherein the side arm is removable.

13. The ingestible capsule of claim 9, wherein the flex foil partially unfolds along at least one folding line when the movable piston is actuated to empty the drug reservoir.

14. The ingestible capsule of claim 1, wherein the flex foil comprises a circuit board and the electronic components are formed directly on the circuit board without a rigid circuit board.

15. An ingestible capsule comprising:
    a housing defining one or more compartments; and
    a bent flex foil disposed in one of the compartments, the bent flex foil comprising a plurality of electronic components disposed directly on a continuous, flexible circuit board and further comprising an antenna formed as an oblique extension of the flexible circuit board, wherein the flexible circuit board is bent along bend lines disposed between the plurality of electronic components and the antenna is bent relative to the remainder of the flexible circuit board.

16. The ingestible capsule of claim 15, wherein each of the plurality of electronic components is free of a rigid circuit board.

17. The ingestible capsule of claim 15, wherein the antenna comprises an electrically conducting layer integrated into the flexible circuit board.

18. The ingestible capsule of claim 15, wherein at least one of the plurality of electronic components is attached to the flexible circuit board using a solder bump.

19. The ingestible capsule of claim 15, wherein a moldable resin fixes at least one of the plurality of electronic components to the flexible circuit board.

20. The ingestible capsule of claim 15, wherein the electronic components comprise at least one of a capacitor and a coil.

* * * * *